(12) United States Patent
Makinoda

(10) Patent No.: US 8,183,205 B2
(45) Date of Patent: May 22, 2012

(54) GRANULOCYTE COLONY STIMULATING FACTOR FOR THE TREATMENT OF AN OVULATION DISORDER CAUSED BY LUTEINIZED UNRUPTURED FOLLICLE

(75) Inventor: Satoru Makinoda, Kanazawa-shi, Ishikawa (JP)

(73) Assignee: Satoru MAKINODA, Ishikawa (JP)

( * ) Notice: Subject to any disclaimer, the term of this patent is extended or adjusted under 35 U.S.C. 154(b) by 12 days.

(21) Appl. No.: 12/615,035

(22) Filed: Nov. 9, 2009

(65) Prior Publication Data

US 2010/0113336 A1    May 6, 2010

Related U.S. Application Data

(62) Division of application No. 11/682,054, filed on Mar. 5, 2007, now abandoned.

(51) Int. Cl.
*A61K 38/00* (2006.01)

(52) U.S. Cl. .................... 514/7.7; 514/9.8; 514/10.5

(58) Field of Classification Search .................. None
See application file for complete search history.

(56) References Cited

OTHER PUBLICATIONS

Randall and Templeton, Hum. Reprod. 1991; 6(5): 659-664.*
Zaidi et al., Human Reproduction, 1995; 10: 44-49.*
Translation of Hirosaki dopument by STIC; 25 pages, (Kanazawa Ika Daigaku Zasshi), (Dec. 2006), 31 (4).
Hirosaki (Kanazawa Ika Daigaku Zasshi (Dec. 2006),31(4),274-280; article in Japanese.
English language abstractfor Hirosaki (Kanazawa Ika Daigaku Zasshi (Dec. 2006), 31 (4), 274-280); 2 pages.
Acta Obst. Gynaec Jpn., vol. 47, No. 5, pp. 493-494 (1995).
Newsletter of Tohoku Society of Obstetrics and Gynecology, No. 46, pp. 55-56 (1999).
Kanazawa Med. Univ., vol. 24, pp. 42-49 (1999).
Kanazawa Med. Univ., vol. 25, pp. 228-233 (1999).
Med. J. Noto General Hosp., vol. 11, pp. 4-11 (2000).
JAOG News (supplement), p. 4 (2001).
Human Reproduction, vol. 17, No. 12, pp. 3046-3052 (2002).
Salmassi, Ali et al., Fertility and Sterility, vol. 81, Suppl. 1, pp. 786-791 (2004).
Acta Obstetrica et Gynaecolgica Japonica, vol. 58, No. 2, p. 171 (S-23) (2006).
Acta Obstetrica et Gynaecolgica Japonica, vol. 58, No. 2, p. 174 (S-26) (2006).
Acta Obstetrica et Gynaecolgica Japonica, vol. 58, No. 2, p. 292 (S-144) (2006).
Makinoda, Satoru, Acta Obstetrica et Gynaecolgica Japonica, vol. 58, No. 9, p. N-352-356 (2004).

* cited by examiner

*Primary Examiner* — Bridget E Bunner
*Assistant Examiner* — Christina Borgeest
(74) *Attorney, Agent, or Firm* — Fitch, Even, Tabin & Flannery, LLP

(57) ABSTRACT

A therapeutic agent for ovulation disorder of the present invention is characterized in comprising Granulocyte colony-stimulating factor; and that the ovulation disorder is caused by Luteinized Unruptured Follicle.

9 Claims, 2 Drawing Sheets

GRANULOCYTE COLONY STIMULATING FACTOR FOR THE TREATMENT OF AN OVULATION DISORDER CAUSED BY LUTEINIZED UNRUPTURED FOLLICLE

This is a divisional application of U.S. application Ser. No. 11/682,054, filed on Mar. 5, 2007, the complete disclosure of which is incorporated by reference.

BACKGROUND OF THE INVENTION

1. Field of the Invention

This invention relates to a therapeutic agent for ovulation disorder caused by Luteinized Unruptured Follicle, and a method for treating ovulation disorder caused by Luteinized Unruptured Follicle.

2. Description of the Related Art

In menstrual cycle, a menstruation and an ovulation are repeated every month for forthcoming pregnancy. This phenomenon is controlled by various hormones such as hypothalamic hormones, pituitary hormones and ovarian hormones, and the mechanism is almost elucidated. However, the local mechanism in ovary that an ovarian follicle grows up to 20 mm in only 14 days and ruptures at 36 hours after Lutenizing Hormone (LH) surge is still obscure.

In 1960, Espey proposed the hypothesis that ovulation is an inflammatory-like reaction.

Based on this hypothesis, the inventor and researchers in his department had studied the relation between ovulation and inflammatory cytokines such as TNF-$\alpha$, IL-1$\beta$, IL-6 for several years. As a result, it was clarified that 1) peripheral serum concentration of Granulocyte Colony-Stimulating Factor (hereinafter referred to as G-CSF) shows a peak at a few days before ovulation, 2) the concentration of the other inflammatory cytokines reveal no significant changes in peripheral serum, 3) G-CSF shows the highest follicular fluid/serum concentration ratio at oocyte pick up in IVF procedure among the tested cytokines, and 4) G-CSF mRNA in the follicular wall increases 10 fold at late luteal phase compared to the other phases in menstrual cycle. Moreover, the inventor and researchers in his department suggested the possibility of G-CSF as a therapeutic agent for ovulation disorders, although it was not clear which kinds of ovulation disorders was G-CSF effective for at that time.

The inventor and researchers in his department published these results in Acta Obst Gynaec Jpn, Vol. 47, No. 5, pp. 493-494 (1995); Newsletter of Tohoku Society of Obstetrics and Gynecology, No. 46, pp. 55-56 (1999); J. Kanazawa Med. Univ., Vol. 24, pp. 42-49 (1999); J. Kanazawa Med. Univ., Vol. 25, pp. 228-233 (1999); Med. J. Noto General Hosp., Vol. 11, pp. 4-11 (2000); JAOG News (supplement), p. 4 (2001); Human Reproduction, Vol. 17, No. 12, pp. 3046-3052 (2002).

It is described in Ali Salmassi, et al., Fertility and Sterility, Vol. 81, Suppl. 1, pp. 786-791 (2004) by the other research group that 1) G-CSF concentration in the follicular fluid is significantly higher than that of serum, and 2) G-CSF and its receptor is located in the luteinized granulose cells. However, these results had been already reported by the inventor and researchers in his department.

In normal menstrual cycle, follicular growth and maturation, ovulation, formation and regression of corpus luteum are repeated periodically. In contrast, there is an ovulation disorder that lutenization without ovulation is observed after follicular growth and maturation. This disorder is called as Luteinized Unruptured Follicle (hereinafter referred to as LUF), and is observed even in normal women. LUF is more commonly observed at the use of some kinds of agents for ovulation induction at the rate of 20% and its recurrence rate is 78.6%. Thus, LUF is an ironical and serious disorder that ovulation induction causes unovulation.

SUMMARY OF THE INVENTION

As mentioned above, the inventor and researchers in his department have diligently studied about the relation of ovulation and G-CSF. As a result, the inventor found that G-CSF is excellently effective for treating ovulation disorder caused by LUF, and completed the present invention.

A therapeutic agent for ovulation disorder of the present invention is characterized in comprising Granulocyte colony-stimulating factor; and that the ovulation disorder is caused by Luteinized Unruptured Follicle.

A method for treating ovulation disorder of the present invention is characterized in comprising the step of administering the agent of the present invention.

DETAILED DESCRIPTION OF PREFERRED EMBODIMENTS OF THE INVENTION

Figure 1:
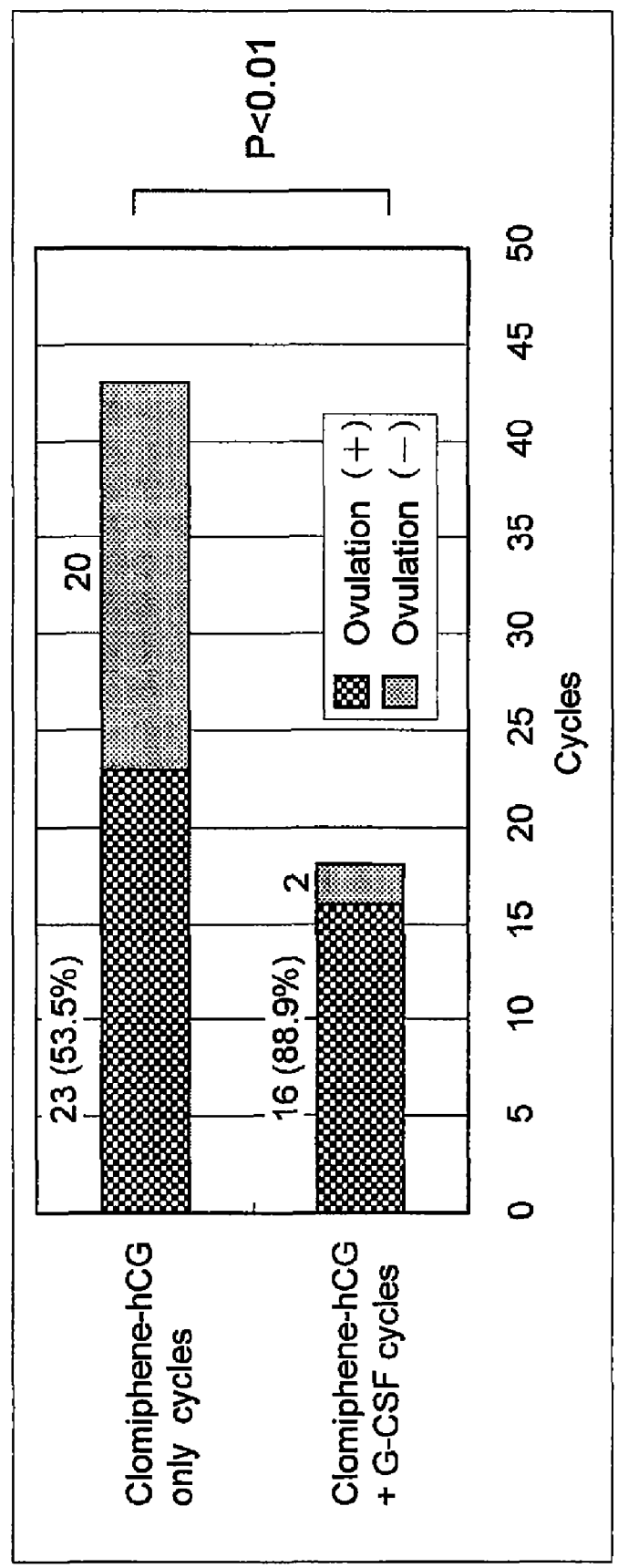
FIG. 1 shows the comparison of ovulation rates and number of ovulated cycles between Clomiphene-hCG treatment only and the administration of G-CSF in addition of Clomiphene-hCG treatment.
Figure 2:
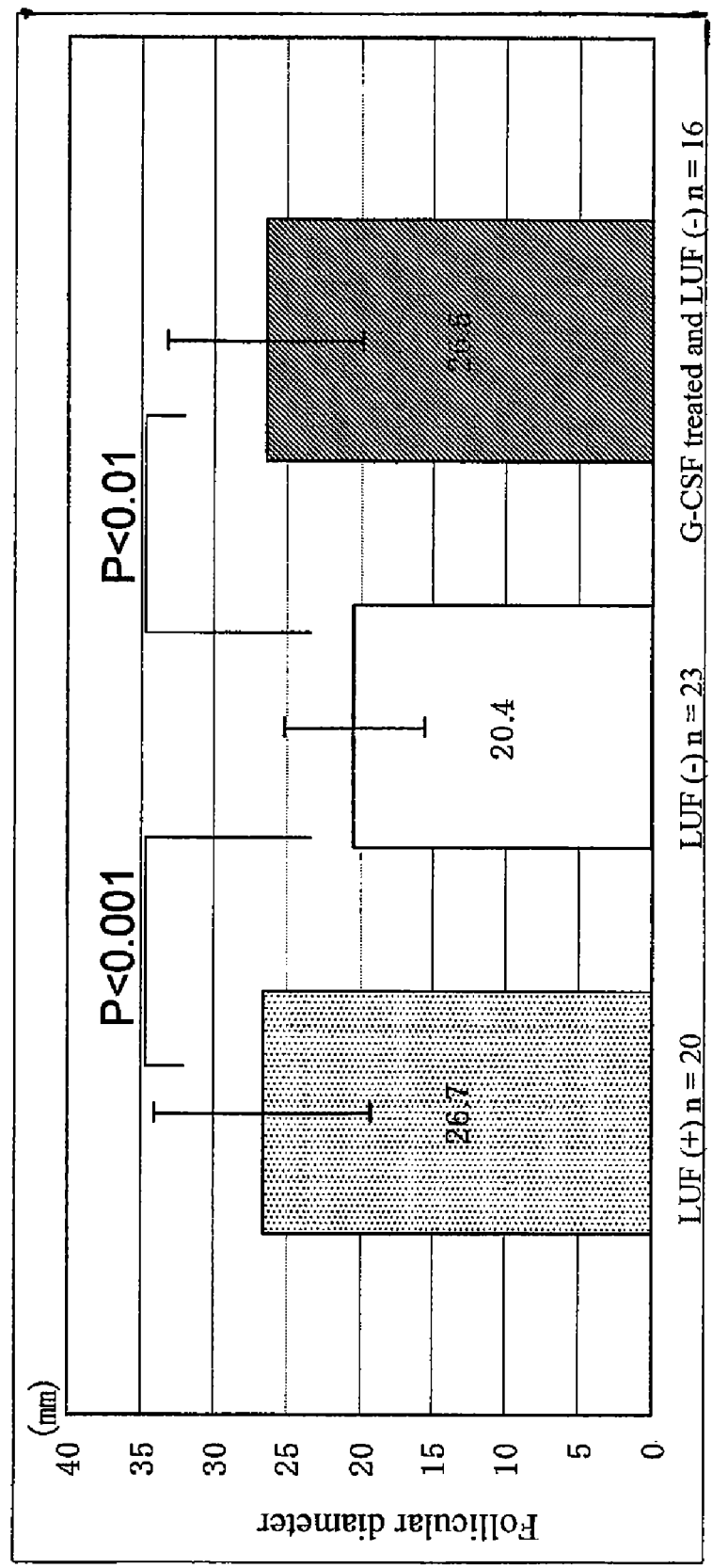
FIG. 2 shows the comparison of the follicular diameters of LUF cycles, normal ovulated cycles, and ovulated cycles treated by G-CSF based on this invention.

The therapeutic agent for ovulation disorder of the present invention comprises Granulocyte colony-stimulating factor (G-CSF) as a main active component.

G-CSF is one of the hematopoietic cytokines and induces bone marrow cells to granulocytes. For this reason, G-CSF is widely used to increase the number of granulocyte in anti-cancer chemotherapy. In addition, G-CSF is also used for the treatment of aplastic anemia, for donors of bone marrow transplantation, or the like.

In the present invention, any type of G-CSF can be used, such as commercially available G-CSF and G-CSF produced by recombinant DNA technology. In the technology, vector having a gene coding G-CSF and promoter is prepared at first. Then, appropriate cells are transfected by the vector. After the culture of the cells, the cells are homogenized, and the fraction containing proteins is obtained by conventional method such as centrifugation. G-CSF can be purified from the fraction by conventional method. If it is necessary, SS-bridge is formed by oxidizing agent.

The dosage form of the therapeutic agent of the present invention is not specified. Preferably, injectable form is recommended, since G-CSF as main active component is a peptide. In such a case, pH-corrected physiological saline solution or isotonic glucose solution can be used as a solvent Pure water, distilled water and sterilized water can be a solvent for freeze-dried G-CSF with salts. The concentration of G-CSF in such an injectable solution may be similar to the concentration of ordinary injectable solution, and may be, for example, about 50 to 400 µg/mL. The injectable solution needs to be isotonic.

As a method for ovulation disorder, Clomiphene treatment, Clomiphene-human Chorionic Gonadotropin (hCG) treatment and human Menopausal Gonadotropin (hMG)-hCG treatment are used conventionally.

In Clomiphene treatment, 50 to 100 mg/day of Clomiphene citrate is orally administered for about 5 days from 5th day after menstruation. In Clomiphene-hCG treatment, 5000 to 10000 IU of hCG is intramuscularly injected when the diameter of dominant follicle reaches 18 mm, in addition to the administration of Clomiphene. In hMG-hCG treatment, hMG is administered for about 10 days to maturate ovarian follicle, and hCG is injected when the diameter of dominant follicle reaches 18 mm.

In these conventional treatments, especially in Clomiphene-hCG treatment, the incidence of LUF increases significantly more than in normal menstrual cycles. The inventor has observed the effectiveness of G-CSF administration on the treatment of LUF.

An ovarian follicle usually luteinizes after an egg is released from a matured ovarian follicle. However, a matured ovarian follicle sometimes luteinizes without releasing an egg. This phenomenon is called as LUF.

LUF is sometimes triggered by fertility drug. The inventor has found that the administration of G-CSF is effective for the suppression of LUF, especially LUF caused by fertility drug such as Clomiphene.

The method for treating ovulation disorder according to the present invention can improve an ovulation disorder caused by LUF, and is characterized in comprising the step of administering the therapeutic agent of the present invention. Specifically, G-CSF is administered 1 or 2 days before the size of ovarian follicle reaches 18 mm, while an egg is released when the size of ovarian follicle reaches about 20 to 25 mm. Alternatively, G-CSF is administered 1 or 2 days before hCG injection in the conventionally method in which hCG is used. Exact time to administer G-CSF can be decided based on the transvaginal ultrasonography for monitoring the growth status of follicles.

The dose of G-CSF in the treatment may be adjusted depending on the condition and age of the patient and the like, and is usually 50 to 200 μg per one administration. Though the number of times of doses is usually once per one menstrual cycle, multiple administrations per one menstrual cycle are also approved. Since G-CSF is a peptide, subcutaneous or intravenous injection is recommended.

EXAMPLES

The present invention will be explained more specifically by examples below. However, the present invention is not limited by the following examples, and necessary alterations can be made on the present invention to an extent applicable to the above-described and later-described points. All of them are included in the technical scope of the present invention.

Example 1

(1) Participants

G-CSF was administered to 16 adult women participants who met the following requirements:

(a) Infertile patients at Kanazawa Medical University and affiliated hospitals, who were treated by Clomiphene-hCG treatment and confirmed to have LUF by the monitoring of basal body temperature and transvaginal ultrasonography during the period from March to November, 2006;
(b) Patients who received the explanation of the trial and agreed to the clinical trial;
(c) Patients whose ages were under forty years old;
(d) Patients who had no severe adhesion around ovaries;
(e) Patients who were treated by the same ovulation induction treatment in the clinical trial as the treatment which had given to the patients just before the clinical trial;
(f) Patients whose number of peripheral leukocyte was 10,000/μL or less;
(g) Patients who had no allergy and drug hypersensitivity;
(h) Patients who had no severe disorder in lever, kidney, and heart; and
(i) Patients who were approved to participate in the clinical trial by a doctor.

(2) Pre-Trial Observation

Age of the 16 participants, duration of infertility, and the number of treated menstrual cycles were 3.3.3±3.1 years old, 35.2±20.5 months, and 10.2±7.3 menstrual cycles, respectively.

By the laparoscopic observation before the clinical trial, the following diseases in Table 1 were observed in the 16 participants.

TABLE 1

|  | Number | Ratio(%) |
|---|---|---|
| Endometriosis | 9/16 | 56.3 |
| Myoma uteri | 4/16 | 25.0 |
| Slight adhesion around ovaries | 3/16 | 18.3 |
| Polycystic ovarian syndrome | 2/16 | 12.5 |
| Small tubal fimbria | 2/16 | 12.5 |
| Narrowed tube | 1/16 | 6.3 |

In these 16 participants, the incidence of LUF was examined in a total of 61 menstrual cycles. The incidence of LUF was observed in 23 cycles (37.7%) out of a total of 61 cycles. In 12 menstrual cycles in which fertilization treatment was not provided, the incidence of LUF was observed in 1 menstrual cycle (8.3%), and the incidence of LUF was not observed in 11 menstrual cycles (91.7%). In 43 menstrual cycles in which Clomiphene-hCG treatment was provided, the incidence of LUF was observed in 20 menstrual cycles (46.5%) In 6 menstrual cycles in which hMG-hCG treatment was provided, the incidence of LUF was observed in 2 menstrual cycles (33.3%). These results are arranged in Table 2. As shown in Table 2, the incidence ratio of LUF in case when Clomiphene-hCG treatment or hMG-hCG treatment is provided is clearly higher than that in case of no these treatments. Especially, the incidence ratio of LUF in case of Clomiphene-hCG treatment is high. The incidence ratio of LUF in case of Clomiphene-hCG treatment is significantly high compared to the ratio without fertilization treatment by $P<0.05$ by Fisher's test.

TABLE 2

|  | LUF(+) | | LUF(−) | |
|---|---|---|---|---|
|  | number | ratio | number | ratio |
| Without fertilization treatment | 1/12 | 8.3% | 11/12 | 91.7% |
| Clomiphene-hCG treatment | 20/43 | 46.5% | 23/43 | 53.5% |
| hMG-hCG treatment | 2/6 | 33.3% | 4/6 | 66.7% |

(3) Administration of G-CSF

G-CSF was administered to the 16 participants in 18 menstrual cycles. Only one participant took the administration of G-CSF in 3 menstrual cycles. At first, 50 to 100 mg/day of Clomiphene citrate was orally administered from 5th day after first day of menstruation for 5 days. The growth status of ovarian follicle was observed by transvaginal ultrasonography. In conventional Clomiphene-hCG treatment, 5,000 to 10,000 IU of hCG, which has luteinizing hormone like action, is administered when the diameter of dominant follicle reached 18 mm. In G-CSF treatment cycles, 100 μg of G-CSF was administered subcutaneously 1 or 2 days before hCG injection, in consideration of the disposition of G-CSF in peripheral blood. The disposition of G-CSF in peripheral blood is disclosed by the researches in the inventor's department in J. Kanazawa Med. Univ., Vol. 24, pp. 42-49, (1999); and Human Reproduction, Vol. 17, No. 12, pp. 3046-3052, (2002).

Whether ovulation had occurred or not was estimated by the observation of the disappearance of ovarian follicle by transvaginal ultrasonography within a week after hCG injection, since ovulation is usually observed at about 36 hours after hCG administration.

(4) Result

In Clomiphene-hCG treatment without G-CSF administration, the number of menstrual cycles in which ovulation was observed was 23 out of 43 menstrual cycles, and the ovulation rate was only 53.5%. On the other hand, in case that G-CSF was administered in addition to Clomiphene-hCG treatment, the number of menstrual cycles in which ovulation was observed was 16 out of 18 menstrual cycles, and the ovulation rate was 88.9%. These results were examined by Fisher's test. The incidence of LUF was significantly suppressed in G-CSF administration cycles compared to Clomiphene-hCG treatment cycles at $p<0.01$. These results are shown in FIG. 1.

The diameters of ovarian follicle just before ovulation or hCG injection were compared as hereinafter described. In Clomiphene-hCG treatment cycles without the administration of G-CSF, the diameter of ovarian follicle just before ovulation or hCG injection was 26.7±7.5 mm in 23 menstrual cycles in which LUF was observed, and the diameter was 20.4±4.9 mm in 38 menstrual cycles in which LUF was not observed. The diameter of ovarian follicle just before ovulation was 26.5±6.7 mm in 16 menstrual cycles in which ovulation was occurred by G-CSF administration. These results were examined by Welch's t-test. In Clomiphene-hCG treatment cycles without the administration of G-CSF, the diameters of ovarian follicle in the menstrual cycles in which LUF was observed were significantly larger than that in the menstrual cycles in which LUF was not observed at $P<0.001$, so it was appeared that LUF tends to occur in case that the diameter of ovarian follicle just before ovulation is large, as shown in FIG. 1. A significant difference was not shown between the diameter in the menstrual cycles in which LUF was observed and the diameter in the menstrual cycles in which LUF was not observed by $P=0.9$. In menstrual cycles in which G-CSF was administered, ovulation was observed even when the diameters of ovarian follicle were large.

As shown the above result, it is obvious that ovulation disorder is dominantly improved by the administration of G-CSF, even when the administration of fertility drug adversely affects to induce LUF.

What is claimed is:

1. A method for treating a patient in need of treatment for an ovulation disorder caused by Luteinized Unruptured Follicle, comprising the step of administering a therapeutic agent comprising granulocyte colony-stimulating factor to said patient.

2. The method according to claim 1, wherein the Luteinized Unruptured Follicle is caused by a fertility drug.

3. The method according to claim 2, wherein the fertility drug is clomiphene or a pharmaceutically acceptable salt thereof.

4. The method according to claim 3, wherein the fertility drug is clomiphene citrate.

5. The method according to claim 1, wherein the therapeutic agent is administered as an injectable solution.

6. The method according to claim 5, wherein the injectable solution contains granulocyte colony-stimulating factor in a concentration of about 50 μg/mL to 400 μg/mL.

7. The method according to claim 1, wherein the therapeutic agent is administered 1 or 2 days before the size of dominant ovarian follicle reaches 18 mm.

8. The method according to claim 7, wherein the therapeutic agent is administered 1 day before the size of dominant ovarian follicle reaches 18 mm.

9. The method according to claim 7, wherein the therapeutic agent is administered 2 days before the size of dominant ovarian follicle reaches 18 mm.

* * * * *